United States Patent [19]

Cale, Jr. et al.

[11] 4,133,881
[45] Jan. 9, 1979

[54] AZETIDINYL ACETONITRILE AND ACETAMIDE ANTIARRHYTHMIA COMPOSITIONS AND METHODS

[75] Inventors: Albert D. Cale, Jr., Mechanicsville; Herndon Jenkins, Richmond, both of Va.

[73] Assignee: A. H. Robins Company, Incorporated, Richmond, Va.

[21] Appl. No.: 791,431

[22] Filed: Apr. 27, 1977

[51] Int. Cl.² .................. A61K 31/44; A61K 31/395; C07D 401/06; C07D 205/04
[52] U.S. Cl. .................. 424/244; 260/239 A; 424/263; 546/275
[58] Field of Search ....... 260/239 A, 293.69, 295 CA, 260/294.9; 424/244, 263

[56] References Cited

U.S. PATENT DOCUMENTS 3,318,869  5/1967  Cusic .............................. 260/293.54

FOREIGN PATENT DOCUMENTS 2548053  5/1976  Fed. Rep. of Germany ...... 260/239 A

OTHER PUBLICATIONS

Higgins et al., Chem. Abs. 77, 126337y (1972).

*Primary Examiner*—Jose Tovar
*Assistant Examiner*—Mark L. Berch

[57] ABSTRACT

α-(1-R-3-Azetidinyl)-α-phenyl-α-substituted-acetamides and -acetonitriles represented by the following formula:

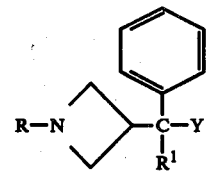

wherein R represents hydrogen, lower alkyl, lower cycloalkyl or phenyllower alkyl, $R^1$ represents phenyl or 2-pyridyl, and Y is carbamoyl or cyano having antiarrhythmic activity are disclosed. Pharmaceutically acceptable acid addition salts of the free bases and quaternary salts are included as part of the invention.

36 Claims, No Drawings

AZETIDINYL ACETONITRILE AND ACETAMIDE ANTIARRHYTHMIA COMPOSITIONS AND METHODS

BACKGROUND OF THE INVENTION

1. FIELD OF INVENTION

The present invention relates to certain heterocyclic organic compounds which may be referred to as $\alpha,\alpha,\alpha$-trisubstituted acetamides and acetonitriles and is more particularly concerned with $\alpha$-(1-R-3-azetidinyl)-$\alpha$-phenyl-$\alpha$-substituted acetamides and acetonitriles, compositions containing the same as active ingredients and methods of using them to control cardiac arrythmia.

2. DESCRIPTION OF THE PRIOR ART

The prior art discloses $\alpha$-(1-R-3-pyrrolidinyl)-$\alpha,\alpha$-diphenylacetamides (and -acetonitriles) and $\alpha$-(1-R-3-pyrrolidinyl)-$\alpha$-phenyl-$\alpha$-(2-pyridyl)acetamides (and -acetonitriles) in U.S. Pat. Nos. 3,192,206; 3,192,210; 3,192,221; 3,102,230, and 4,002,766.

SUMMARY OF INVENTION

The present invention is especially concerned with heterocyclic organic compounds, compositions containing said compounds as active ingredients and methods of using said compositions in controlling cardiac arrhythmias, said compounds having the formula:

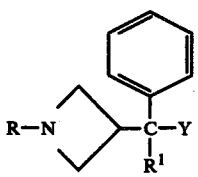

Formula I wherein;
R is hydrogen, lower alkyl, lower cycloalkyl, or phenyl-lower alkyl;
$R^1$ is phenyl or 2-pyridyl, and
Y is carbamoyl or cyano.

The pharmaceutically acceptable acid addition salts and the quaternary salts of Formula I are within the purview of the present invention.

DESCRIPTION OF THE PREFERRED EMBODIMENTS

The compounds described hereinafter and represented by the foregoing Formula I have been shown by accepted pharmacological procedures to have utility as physiologically active agents, and particularly, as effective antiarrhythmic agents therapeutically applicable in the treatment of cardiac arrhythmias. Certain of the compounds of Formula I may also be utilized to prepare other compounds of Formula I as exemplified hereinafter.

The antiarrhythmic activity of the novel compounds of the present invention was demonstrated using the following procedure. Adult mongrel dogs of either sex weighing from 8 to 14 kg. were used under barbiturate anesthesia. A Grass Model 7 polygraph was used for recording femoral arterial blood pressure (Statham P23AC Transducer) and the electrocardiogram (Grass 7P4 Preamplifier). Ouabain was given intravenously in an initial dose of 40$\gamma$/kg., in a second dose of 20$\gamma$/kg. given 30 minutes after the first dose, and in subsequent doses of 10$\gamma$/kg. which were repeated at 15 minute intervals as required for producing cardiac arrhythmias that persisted for at least 15 minutes. When the arrhythmias were established the test compounds were administered by infusion (Harvard Model 942 infusion pump) into a femoral vein at a rate of 1 mg/kg/min. Concentrations of compounds were adjusted according to the weight of the dog to allow a volume infusion of 1 ml/min. Compounds that are considered to be active as antiarrhythmic agents elicit reversion of the arrhythmia to sinus rhythm.

It is, accordingly, an object of the present invention to provide novel azetidinyl compounds possessing antiarrhythmic activity. An additional object is the provision of azetidinyl compounds having antiarrhythmic activity and which produce minimal side effects. A further object is to provide pharmaceutical compositions containing the azetidinyl compounds as active ingredients. A still further object is to provide a method of using azetidinyl compounds having antiarrhythmic activity in the treatment of living animal and especially mammalian bodies. Additional objects will be apparent to one skilled in the art, and still other objects will become apparent hereinafter.

The invention also includes pharmaceutically acceptable acid addition salts of the above bases and the optical isomers thereof which are formed with non-toxic organic and inorganic acids. Such salts are usually prepared by methods known to the art. The base is reacted with either the calculated amount of organic or inorganic acid in aqueous miscible solvent, such as ethanol or isopropanol, with isolation of the salt by concentration and cooling or with an excess of the acid in an aqueous immiscible solvent, such as ethyl ether or isopropyl ether, with the desired salt separating directly. Exemplary of such organic salts are those with maleic, fumaric, benzoic, ascorbic, tartaric, malic, and citric acid and the like. Exemplary of such inorganic salts are those with hydrochloric, hydrobromic, sulfuric, phosphoric and nitric acids.

Quaternary salts of the organic bases of Formula I are also suitable for controlling cardiac arrhythmias and are prepared using alkyl and aralkyl halides or sulfates. The alkylating radicals can be the same or different than R. When the alkylating radical is different than R, the entering group may approach the azetidine ring from the same side as the 3-azetidinyl substituent, giving rise to a cis configuration, or it may approach from the opposite side, giving rise to a trans configuration. The stereoisomers formed due to quaternization are included within the scope of the present invention.

Stereoisomers are present when $R^1$ is other than phenyl and when R contains an asymmetric carbon atom, two asymmetric sites are present. The stereoisomers and diastereoisomers are also included within the scope of the invention.

In the definitions of symbols in the foregoing Formula I and where they appear elsewhere throughout this specification, the terms have the following significance.

The term "lower-alkyl" as used herein includes straight and branched chain radicals of from 1 to 8 carbon atoms inclusive. Examples of lower-alkyl radicals are methyl, ethyl, propyl, n-butyl, isopropyl, isobutyl, amyl, isoamyl, hexyl, heptyl, octyl, isooctyl, and the like.

The term "lower cycloalkyl" as used herein includes primarily cyclic radicals containing 3 to 9 carbon atoms inclusive and encompasses such groups as cyclopropyl, cyclobutyl, cyclopentyl, cyclohexyl, methylcyclohexyl, propylcyclohexyl, cycloheptyl, and cyclooctyl.

The term "phenyllower-alkyl" as used herein includes groups such as benzyl, phenethyl, 1-phenylethyl, phenpropyl, and the like.

The novel compounds of the present invention are prepared according to the following reaction scheme:

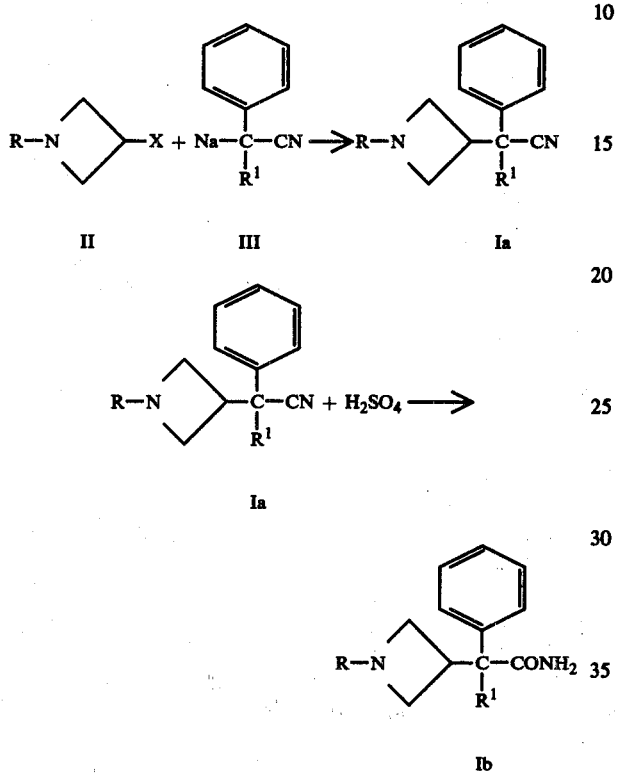

wherein R and R¹ have the values assigned hereinabove, Y of Formula I is shown as —CN and —CONH₂ and X is —OSO₂CH₃ (mesyloxy) or halide.

The processes illustrated above are carried out as described more fully hereinafter in the examples which follow. In general, an α-phenyl-α-substituted acetonitrile is first metalated in a dry aprotic solvent using sodium hydride or sodamide to give a sodio α-phenyl-α-substituted acetonitrile (III) which is allowed to react with a selected 1-R-3-mesyloxy or a halo-acetidine (II) to give an α-(1-R-3 azetidinyl)-α-phenyl-α-substituted acetonitrile (Ia). The α-(1-R-3-azetidinyl)-α-phenyl-α-substituted acetamides (Ib) are prepared by acid hydrolysis of the precursor nitriles. Compounds of Formula Ia and Ib are within the definition of Formula I.

The condensation with the 3-substituted acetidine (II) is usually carried out with the application of heat, e.g., in refluxing benzene, toluene, or like solvent for an extended period, e.g., approximately three hours. The solvent (e.g., toluene) solution is then washed with water and the product extracted with mineral acid as, for example, one normal hydrochloric acid. The aqueous acid extract is basified as with dilute sodium hydroxide solution, the basic solution extracted with a water-insoluble solvent such as ether or chloroform, the solution washed and dried, as over sodium sulfate, concentrated, and the residue distilled in vacuo or crystallized.

The acetamides (Ib) are prepared by heating the 1-R-3-azetidinyl-α-phenyl-α-substituted acetonitriles (Ia) in concentrated sulfuric acid for a period of from about 15 hours to about 60 hours at a temperature of from about 50° C. to about 80° C., preferably at 60° C. to 70° C. The acidic mixture is cooled and maintained below about 50° C. while the solution is basified using a strongly basic solution as, for example, 50% sodium hydroxide; the acetamide products (Ib) are extracted with a suitable solvent such as chloroform or ethyl acetate, the extract concentrated and the products allowed to separate from the concentrated solutions.

Compounds of Formula Ib wherein R is hydrogen are prepared by shaking a compound wherein R is 1-phenylethyl in about three atmospheres of hydrogen using a palladium-on-charcoal (Pd/C) catalyst.

Compounds of Formula Ib wherein R is methyl are prepared by quaternizing the 1-phenylethyl compound with methyl bromide and then removing the 1-phenylethyl group by hydrogenolysis at room temperature using Pd/C as catalyst in the presence of potassium hydroxide.

Compounds of Formula I wherein R is H are employed to prepare other compounds of Formula I by reaction with appropriate R-halide compounds.

Starting materials of Formula II wherein X = —OSO₂CH₃ and R is other than hydrogen are preferably prepared in a benzene solution as follows:

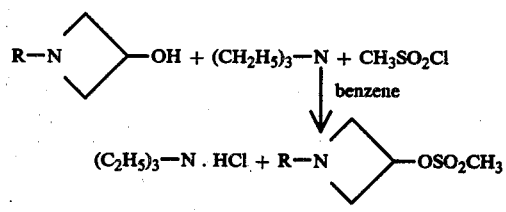

The triethylamine hydrochloride precipitates and is removed by filtration leaving the 1-R-3-azetidinyl mesylate (II) in benzene solution. Starting materials of Formula III are preferably prepared in toluene solution, and the benzene solution of the mesylate (II) added to the refluxing toluene solution of a compound of Formula III. Preparation of 1-substituted-3-azetidinols and mesylates is described in Chem. Pharm. Bull. Vol. 22 (7), pages 1490-1497 (1974). Preparations for 1-alkyl-3-azetidinols, including 1-methyl-3-acetidinol, are given in German Offen. 1,932,219.

Starting material of Formula II wherein X = Cl and R is methyl is prepared according to Preparation 1.

Preparation 1

3-Chloro-1-methylazetidine Hydrochloride.

A mixture of dilute sodium hydroxide solution and 700 ml. of toluene was used to partition 46 g. (0.134 mole) of 3-diphenylmethoxy-1-methylazetidine oxalate. The toluene solution was dried over anhydrous sodium sulfate and further dried by azeotropic distillation of toluene to 300 ml. final volume. The dried toluene solution was treated with 10% palladium-on-charcoal and hydrogenated at 45 p.s.i. at 80° C. for 5 hours. The mixture was filtered and 41 g. (0.264 mole) of carbon tetrachloride was added to the filtrate. After cooling the resulting solution in an ice-methanol bath, 53.5 g. (0.145 mole) of trioctylphosphine was added in one portion with stirring. The temperature rose rapidly to a maximum of 50° C. The solution was stirred for 30 minutes and distilled to a pot temperature of 150° C. The distillate was acidified with ethereal hydrogen chloride. The resulting crystals were separated by filtration and dried in vacuo to give 8.5 g. of product (45%).

The invention further provides pharmaceutical compositions comprising, as active ingredient, at least one of the compounds according to the invention in association with a pharmaceutical carrier or excipient. The compounds may be presented in a form suitable for oral, parenteral or intracardial administration, or in a form suitable for inhalation. Thus, for example, compositions for oral administration are solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed antiarrhythmic effective dose of active ingredient. Although very small quantities of the active materials of the present invention are effective when minor therapy is involved or in cases of administration to subjects having a relatively low body weight, unit dosages are usually from 5 milligrams or above and preferably 25, 50 or 100 milligrams or even higher, depending of course upon the emergency of the situation and the particular result desired. Five to 50 milligrams appears optimum per unit dose, or usual broader ranges appear to be 1 to 100 milligrams per unit dose. Daily dosages should preferably range from 10 mg. to 100 mg. It is only necessary that the active ingredient constitute an effective amount, i.e., such that a suitable effective dosage will be obtained, consistent with the dosage form employed. Obviously, several unit dosage forms may be administered at about the same time.

| CAPSULES | |
|---|---|
| Ingredients | Per Cap., mg. |
| 1. Active ingredient | 5.0 |
| 2. Lactose | 140.0 |
| 3. Magnesium stearate | 4.0 |

Procedure:
(1) Blend 1, 2 and 3.
(2) Mill this blend and blend again.
(3) This milled blend is then filled into No. 1 hard gelatin capsules.

| TABLETS | |
|---|---|
| Ingredients | Mg./tabl., mg. |
| 1. Active ingredient | 5.0 |
| 2. Corn starch | 20.0 |
| 3. Kelacid | 20.0 |
| 4. Keltose | 20.0 |
| 5. Magnesium stearate | 1.5 |

Procedure:
(1) Blend 1, 2, 3 and 4.
(2) Add sufficient water portionwise to the blend from step No. 1 with careful stirring after each addition. Such additions of water and stirring continue until the mass is of a consistency to permit its conversion to wet granules.
(3) The wet mass is converted to granules by passing it through the oscillating granulator, using 8-mesh screen.
(4) The wet granules are then dried in an oven at 140° F.
(5) The dried granules are then passed through an oscillating granulator, using a 10-mesh screen.
(6) Lubricate the dry granules with 0.5% magnesium stearate.
(7) The lubricated granules are compressed on a suitable tablet press.

| INTRAVENOUS INJECTION | |
|---|---|
| Ingredients: | |
| 1. Active ingredient | mg. 5.0 |
| 2. pH 4.0 buffer solution, q.s. to | ml. 1.0 |

Procedure:
(1) Dissolve the active ingredient in the buffer solution.
(2) Aseptically filter the solution from step No. 1.
(3) The sterile solution is now aseptically filled into sterile ampoules.
(4) The ampoules are sealed under aseptic conditions.

| INTRAMUSCULAR INJECTION | |
|---|---|
| ingredients: | |
| 1. Active ingredient | mg. 5.0 |
| 2. Isotonic buffer solution 4.0, q.s. to | ml. 2.0 |

Procedure:
(1) Dissolve the active ingredient in the buffer solution.
(2) Aseptically filter the solution from step No. 1.
(3) The sterile solution is now aseptically filled into sterile ampoules.
(4) The ampoules are sealed under aseptic conditions.

| INHALATION | |
|---|---|
| Ingredients: | |
| 1. Active ingredient | mg. 100 |
| 2. Alcohol 95%, q.s. | cc. 1.0 |

Procedure:
(1) Dissolve No. 1 and No. 2.
(2) This solution is properly packaged in an aerosol dispenser containing a metered valve and suitable propellant.

EXAMPLE 1

α,α-Diphenyl-α-(1-isopropyl-3-azetidinyl)acetonitrile

Procedure A. To 250 ml. of triethylamine was added 114 g. (0.4 mole) of 1-isopropyl-3-azetidinyl mesylate oxalate and the mixture was chopped in a blender for about 10 minutes (the mixture has to be cooled at intervals in an ice bath). About 250 ml. of dry toluene was added followed by 77 g. of anhydrous magnesium sulfate and blended for about one minute and the mixture filtered. The filtrate was added over a period of one hour to a refluxing mixture prepared by refluxing 18.5 g. (0.44 mole) of 57% sodium hydride (in mineral oil) and 77.2 g. (0.4 mole) of diphenylacetonitrile in 1500 ml. of dry toluene for 3 hours. The mixture was refluxed 2 hours, cooled and extracted with dilute hydrochloric acid. The organic layer was extracted five times with water and all the aqueous layers combined. The aqueous solution was made basic with sodium hydroxide and extracted with chloroform which was dried (sodium sulfate) and concentrated. The residue was crystallized from isooctane to give 68 g. (58%) of product, m.p. 92°–95° C. Recrystallization from isooctane raised the melting point to 93°–95° C.

Analysis: Calculated for $C_{20}H_{22}N_2$: C,82.72; H,7.64; N,9.65. Found: C,82.72; H,7.73; N,9.55.

Procedure B. A mixture of 40.42 g. (0.96 mole) of 57% sodium hydride and 168 g. (0.87 mole) of diphenylacetonitrile was refluxed in one liter of dry toluene for 3 hours. In a separate flask 100 g. (0.87 mole) of methanesulfonyl chloride was added dropwise at 20° C. to a stirred solution of 100 g. (0.87 mole) of 1-isopropyl-3-azetidinol and 101 g. (1 mole) of triethylamine in 700 ml. dry benzene. The mixture was stirred at 25° C. for 2 hrs. and filtered. The filter cake was washed with benzene. The combined filtrates were added dropwise over a period of about 30 minutes to the prepared refluxing suspension of the sodium salt of diphenylacetonitrile. After refluxing 1.5 hr. the cooled solution was washed with water and extracted with dilute hydrochloric acid followed by extraction with water. The aqueous extracts were combined, made basic with sodium hydroxide and extracted with chloroform. The chloroform solution was dried (sodium sulfate) and concentrated. The residue was crystallized from isooctane to give 142 g. (56%) of product.

EXAMPLE 2

α-(1-Isopropyl-3-azetidinyl)-α-phenyl-α-(2-pyridyl)acetonitrile

To 13.9 g. (0.33 mole) of 57% sodium hydride (mineral oil suspension) in 350 ml. of dry toluene was added dropwise with stirring 58.2 g. (0.3 mole) of α-(2-pyridyl)phenylacetonitrile in 250 ml. of dry toluene while the temperature was maintained at 90°–111° C. The mixture was refluxed for one hour.

A mixture of 84.9 g. (0.3 mole) of 1-isopropyl-3-azetidinyl mesylate oxalate, 200 ml. of triethylamine and 200 ml. of dry toluene was chopped in a blender for 5 minutes and cooled in an ice bath. The mixture was blended another 5 minutes, 85 g. of magnesium sulfate added and blended another 2 minutes. The mixture was filtered and the filtrate was added over a period of 15 minutes to the refluxing suspension prepared above. After one hour of reflux the mixture was cooled and extracted with water. The toluene layer was extracted three times with dilute hydrochloric acid and twice with water. The aqueous layers were combined, made basic with sodium hydroxide and extracted with isopropyl ether. The ether solution was dried (sodium sulfate) and concentrated. The residue was crystallized twice from isooctane to give 18.5 g. (21%) of product melting at 78°–80° C.

Analysis: Calculated for $C_{19}H_{21}N_3$: C,78.32; H,7.26; N,14.42. Found: C,78.27; H,7.30; N,14.28.

EXAMPLE 3

α,α-Diphenyl-α-(1-methyl-3-azetidinyl)acetonitrile

To 4 g. (0.11 mole) sodium amide in 300 ml. toluene was added 21 g. (0.11 mole) of diphenylacetonitrile and the stirred mixture was refluxed in a nitrogen atmosphere for 4 hrs. The heat was removed and a solution of 3-chloro-1-methylazetidine was added at a rate to maintain reflux. The solution was refluxed 4 hrs., allowed to stand overnight, washed with water and extracted with dilute hydrochloric acid. The aqueous acidic layer was made basic with dilute sodium hydroxide and extracted twice with isopropyl ether. The solution was dried (sodium sulfate) and concentrated. The residue was recrystallized from ligroin to give 6.7 g. (27%) of product, m.p. 113°–115° C.

Analysis: Calculated for $C_{18}H_{18}N_2$: C,82.41; H,6.92; N,10.68. Found: C,82.31; H,6.98; N,10.51.

EXAMPLE 4

α-(1-Isopropyl-3-azetidinyl)-α-phenyl-α-(2-pyridyl)acetamide

To 80 ml. of concentrated sulfuric acid preheated to 70° C. was added 15 g. (0.052 mole) of α-(1-isopropyl-3-azetidinyl)-α-phenyl-α-(2-pyridyl)acetonitrile at a rate to maintain 65°–70° C. The solution was heated to 70° C. for 18 hrs. and poured on ice. The mixture was made basic with 50% sodium hydroxide (with ice cooling and extracted with chloroform. The chloroform was dried (sodium sulfate) and concentrated. The residue was crystallized twice from ethyl acetate-isopropyl ether. Yield 6 g. (37%), m.p. 140°–141° C.

Analysis: Calculated for $C_{19}H_{23}N_3O_1$: C,73.76; H,7.49; N,13.58. Found: C,73.57; H,7.51; N,13.34.

EXAMPLE 5

α,α-Diphenyl-α-(1-isopropyl-3-azetidinyl)acetamide

To 80 ml. of concentrated sulfuric acid preheated to 70° C. was added 25 g. (0.86 mole) of α-(1-isopropyl-3-azetidinyl)-α,α-diphenylacetonitrile at a rate to maintain a temperature of 65°–75° C. The solution was heated at 70° C. for 18 hrs. and poured on ice. The mixture was made basic with 50% sodium hydroxide (while cooling with ice) and extracted with chloroform. The chloroform was dried (sodium sulfate) and concentrated. The residue was crystallized from ethyl acetate-ethanol to give 15.7 g. (59%) of product melting at 181°–184° C.

Analysis: Calculated for $C_{20}H_{24}N_2O_1$: C,77.89; H,7.84; N,9.08. Found: C,77.89; H,7.88; N,8.98.

EXAMPLE 6

α,α-Diphenyl-α-(1-cyclohexyl-3-azetidinyl)acetonitrile

Methylene chloride containing 191 g. (1.0 mole) of 1-cyclohexyl-3-azetidinol hydrochloride was extracted with dilute aqueous sodium hydroxide solution and the organic layer separated, dried over sodium sulfate, filtered and concentrated in vacuo. The residue was dissolved in dry benzene and mixed by stirring with 116 g. (1.05 mole) of triethylamine and thereafter cooled with an ice bath. To the cold stirred solution was added dropwise 115 g. of methane sulfonylchloride and stirring was continued at room temperature for three hours and the mixture thereafter filtered. To one liter of dry toluene containing 50.0 g. (1.0 mole) of sodium hydride was added at 45°–50° C., 193 g. (1 mole) of diphenylacetonitrile and the mixture refluxed with stirring for two hours. To this solution the foregoing filtrate was added at a fast dropwise rate. After addition was complete, reflux was continued for two hours and thereafter the solution was stirred overnight. An equivalent volume of isooctane was added and the solution extracted four times with dilute hydrochloric acid solution. The acid layers obtained in each extraction was combined, made basic with a mixture of 50% sodium hydroxide and ice and extracted with chloroform. The chloroform layer was dried, filtered and concentrated in vacuo. The residue was crystallized by adding isopropyl ether and thereafter the solid recrystallized from isopropyl ether to give 58.0 g. (18%) of product melting at 111°–114° C.

Analysis: Calculated for $C_{18}H_{18}N_2$: C,82.41; H,6.92; N,10.68. Found: C,82.31; H,6.98; N,10.51.

EXAMPLE 7

α,α-Diphenyl-α-[1-(1-phenylethyl)-3-azetidinyl-]acetonitrile

To a solution of 67.9 g. (0.67 mole) of triethylamine and 114 g. (0.64 mole) of 1-(1-phenylethyl)-3-azetidinol in 800 ml. of dry benzene was added dropwise 73.6 g. (0.65 mole) of methane sulfonylchloride while cooling in an ice bath. After stirring two hours at room temperature the mixture was filtered. The filtrate was added dropwise over a 40-minute period to a refluxing suspension of the sodium salt of diphenylacetonitrile prepared by refluxing 123.5 g. (0.64 mole) of the nitrile and 28.2 g. (0.7 mole) of 57% sodium hydride in 1 liter of dry toluene for 2.5 hrs. The toluene solution was extracted with dilute hydrochloric acid. The toluene-organic layer was treated with water and a volume of isooctane equal to the toluene layer. The oily layer and aqueous layer were separated together. The toluene layer was washed several times with water. All aqueous layers (and the oil) were combined and basified with dilute sodium hydroxide and extracted with chloroform. The chloroform layer was dried over sodium sulfate and concentrated by distillation. The residue was crystallized from isooctane isopropyl ether to give 94 g. (42%) of product melting 122°–130° C.

Analysis Calculated for $C_{25}H_{24}N_2$: C,85.19; H,6.86; N,7.95. Found: C,84.98; H,6.84; N,7.83.

EXAMPLE 8

α,α-Diphenyl-α-[1-(1-phenylethyl)-3-azetidinyl-]acetonitrile Methobromide

To 70 g. (0.2 mole) of α,α-diphenyl-α-[1-(1-phenylethyl)-3-azetidinyl]acetonitrile in 200 ml. of isobutyl methyl ketone was added 17.5 g. of methylbromide in 800 ml. of the same solvent. The mixture was allowed to stand 4 days and filtered to give 65 g. (72%) of product melting at 205°–208° C.

Analysis: Calculated for $C_{26}H_{27}BrN_2$: C,69.79; H,6.08; N,6.26. Found: C,69.63; H,6.10; N,6.25.

EXAMPLE 9

α,α-Diphenyl-α-(1-methyl-3-azetidinyl)acetonitrile

A solution of 800 ml. of ethanol and 59 g. (0.13 mole) of α,α-diphenyl-α-[1-(1-phenylethyl)-3-azetidinyl-]acetonitrile methobromide was treated with 7.12 g. (0.13 mole) of potassium hydroxide and 0.25 g. of 10% palladium on carbon. The mixture was shaken under initial hydrogen pressure of 45 p.s.i. at ambient temperature for 24 hours. The mixture was filtered and the filtrate concentrated. The residue was crystallized from isooctane to give 21.7 g. (64%) of product melting 112°–115° C.

EXAMPLE 10

α,α-Diphenyl-α-(1-methyl-3-azetidinyl)acetamide Hydrochloride

To 60 ml. of concentrated sulfuric acid preheated to 60° C. was added 21.7 g. (0.082 mole) of α,α-diphenyl-α-(1-methyl-3-azetidinyl)acetonitrile at a rate so as to maintain a temperature of 60°–70° C. The solution obtained was heated to 70° C. for 18 hrs. and extracted with chloroform. The chloroform extract was dried over sodium sulfate and concentrated and the residue crystallized from ethyl acetate-isopropyl alcohol to give 13.8 g. of the free base (60%) melting at 171°–174° C. The base was treated with hydrogen chloride in isobutyl methyl ketone and the salt recrystallized from isopropyl alcohol to give 9 g. of product melting at 182°–185° C.

Analysis: Calculated for $C_{18}H_{21}ClN_2O$: C,68.24; H,6.68; N,8.84. Found: C,67.88; H,6.72; N,8.78.

EXAMPLE 11

α,α-Diphenyl-α-(1-ethyl-3-azetidinyl)acetonitrile

Following the procedure of Example 6 and substituting equal molar amounts of 1-ethyl-3-azetidinol hydrochloride for 1-cyclohexyl-3-azetidinol hydrochloride, the titled compound is obtained.

EXAMPLE 12

α,α-Diphenyl-3-azetidinylacetamide Fumarate

To a suspension of 23 g. (0.062 mole) of α,α-diphenyl-α-[1-(1-phenylethyl)-3-azetidinyl]acetamide in 150 ml. of ethanol solution was added 1.5 g. of 10% palladium hydroxide on carbon. The mixture was hydrogenated at 70° C. and an initial pressure of 45 p.s.i. for 18 hours and filtered. The filtrate was concentrated and the residue dissolved in 150 ml. of isopropyl alcohol. To this was added 7.2 g. (0.062 mole) of fumaric acid. The resulting crystals were recrystallized three times from ethanol to give 3 g. (13%) of product melting at 171°–173° C.

EXAMPLE 13

α,α-Diphenyl-α-[1-(1-phenylethyl)-3-azetidinyl]-acetamide.

To 100 ml. of concentrated sulfuric acid preheated to 70° C. was added with stirring, 50 g. (0.142 moles) of α,α-diphenyl-α-[1-(1-phenylethyl)-3-azetidinyl]-acetonitrile at a rate to maintain a temperature of 65°–70° C. The solution was heated at 72°–75° C. for 18 hours. The acid solution was poured onto ice and thereafter made basic with 50% aqueous sodium hydroxide solution and extracted with chloroform. The chloroform extract was dried over anhydrous sodium sulfate and concentrated by distillation. The residue was crystallized from isopropyl ether to give 28.5 g. (54%) of material melting at 152°–153.5° C. A sample was recrystallized from isopropyl ether-isopropyl alcohol to give the product melting at 153°–154° C.

Analysis: Calculated for $C_{25}H_{26}N_2O$: C, 81.05; H, 7.07; N, 7.56. Found: C,80.83; H, 7.07; N, 7.40.

What is claimed is:

1. A composition for controlling cardiac arrhythmias with minimal side effects, comprising (1) an antiarrhythmic effective amount of between about 1 and 100 mg. of a compound of the formula:

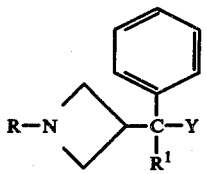

wherein R is hydrogen, lower alkyl, lower cycloalkyl or phenyl-lower alkyl, R¹ is phenyl or 2-pyridyl, Y is carbamoyl, cyano, and pharmaceutically acceptable acid addition salts or quaternary ammonium salts thereof prepared with alkyl and aralkyl halides or sulfates, and (2) a pharmaceutical carrier.

2. A composition of claim 1 wherein R is lower alkyl.

3. A composition of claim 1 wherein the compound is α,α-diphenyl-α-(1-isopropyl-3-azetidinyl)acetamide.

4. A composition of claim 1 wherein the compound is α-(1-isopropyl-3-azetidinyl)-α-phenyl-α-(2-pyridyl)acetamide.

5. A compostion of claim 1 wherein the compound is α,α-diphenyl-α-(1-isopropyl-3-azetidinyl)acetonitrile.

6. A composition of claim 1 wherein the compound is α-(1-isopropyl-3-azetidinyl)-α-phenyl-α-(2-pyridyl)acetonitrile.

7. A composition of claim 1 wherein the compound is α,α-diphenyl-α-(1-cyclohexyl-3-azetidinyl)acetonitrile.

8. A composition of claim 1 wherein the compound is α,α-diphenyl-α-(1-methyl-3-azetidinyl)acetonitrile.

9. A composition of claim 1 wherein the compound is α,α-diphenyl-α-[1-(1-phenylethyl)-3-azetidinyl]acetonitrile methobromide.

10. A composition of claim 1 wherein the compound is α,α-diphenyl-α-(1-methyl-3-azetidinyl)acetamide hydrochloride.

11. A composition of claim 1 wherein the compound is α,α-diphenyl-3-azetidinylacetamide.

12. A composition of claim 1 wherein the compound is α,α-diphenyl-α-[1-(1-phenylethyl)-3-azetidinyl]acetamide.

13. A method of controlling cardiac arrhythmias in a living animal body which comprises administering to said living animal body an antiarrhythmic effective amount of a compound of the formula:

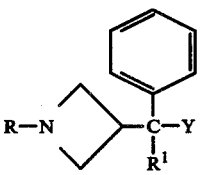

wherein R is hydrogen, lower alkyl, lower cycloalkyl or phenyl-lower alkyl, R¹ is phenyl or 2-pyridyl, Y is carbamoyl, cyano, and pharmaceutically acceptable acid addition salts or quaternary ammonium salts thereof prepared with alkyl and aralkyl halides or sulfates.

14. The method of claim 13 wherein R is lower alkyl.

15. The method of claim 13 wherein the compound is α,α-diphenyl-α-(1-isopropyl-3-azetidinyl)acetamide.

16. The method of claim 13 wherein the compound is α-(1-isopropyl-3-azetidinyl)-α-phenyl-α-(2-pyridyl)acetamide.

17. The method of claim 13 wherein the compound is α,α-diphenyl-α-(1-isopropyl-3-azetidinyl)acetonitrile.

18. The method of claim 13 wherein the compound is α-(1-isopropyl-3-azetidinyl)-α-phenyl-α-(2-pyridyl)acetonitrile.

19. The method of claim 13 wherein the compound is α,α-diphenyl-α-(1-cyclohexyl-3-azetidinyl)acetonitrile.

20. The method of claim 13 wherein the compound is α,α-diphenyl-α-(1-methyl-3-azetidinyl)acetonitrile.

21. The method of claim 13 wherein the compound is α,α-diphenyl-α-[1-(1-phenylethyl)-3-azetidinyl]acetonitrile methobromide.

22. The method of claim 13 wherein the compound is α,α-diphenyl-α-(1-methyl-3-azetidinyl)acetamide hydrochloride.

23. The method of claim 13 wherein the compound is α,α-diphenyl-3-azetidinylacetamide.

24. The method of claim 13 wherein the compound is α,α-diphenyl-α-[1-(1-phenylethyl)-3-azetidinyl]acetamide.

25. A compound selected from α-(1-R-3-azetidinyl)-α-phenyl-α-substituted-acetamides and -acetonitriles of the formula:

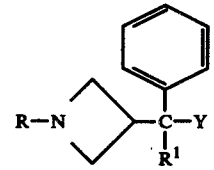

wherein R is hydrogen, lower alkyl, lower cycloalkyl or phenyl-lower alkyl, R¹ is phenyl or 2-pyridyl, Y is carbamoyl or cyano, and pharmaceutically acceptable acid addition salts or quaternary ammonium salts thereof prepared with alkyl and aralkyl halides or sulfates.

26. A compound of claim 25 wherein R is lower alkyl.

27. A compound of claim 25 wherein the compound is α,α-diphenyl-α-(1-isopropyl-3-azetidinyl)acetamide.

28. A compound of claim 25 wherein the compound is α-(1-isopropyl-3-azetidinyl)-α-phenyl-α-(2-pyridyl)acetamide.

29. A compound of claim 25 wherein the compound is α,α-diphenyl-α-(1-isopropyl-3-azetidinyl)acetonitrile.

30. A compound of claim 25 wherein the compound is α-(1-isopropyl-3-azetidinyl)-α-phenyl-α-(2-pyridyl)acetonitrile.

31. A compound of claim 25 wherein the compound is α,α-diphenyl-α-(1-cyclohexyl-3-azetidinyl)acetonitrile.

32. A compound of claim 25 wherein the compound is α,α-diphenyl-α-(1-methyl-3-azetidinyl)acetonitrile.

33. A compound of claim 25 wherein the compound is α,α-diphenyl-α-[1-(1-phenylethyl)-3-azetidinyl]acetonitrile methobromide.

34. A compound of claim 25 wherein the compound is α,α-diphenyl-α-(1-methyl-3-azetidinyl)acetamide hydrochloride.

35. A compound of claim 25 wherein the compound is α,α-diphenyl-3-azetidinylacetamide.

36. A compound of claim 25 wherein the compound is α,α-diphenyl-α-[1-(1-phenylethyl)-3-azetindinyl]acetamide.

* * * * *